(12) United States Patent
Kim et al.

(10) Patent No.: US 7,501,096 B2
(45) Date of Patent: Mar. 10, 2009

(54) SMART PIPETTE FOR CELL MANIPULATION AND CELL MANIPULATION METHOD FOR USING THE SMART PIPETTE

(75) Inventors: Byung-Kyu Kim, Seoul (KR); Young-Ho Kim, Seoul (KR); Deok-Ho Kim, Seoul (KR); Jong-Oh Park, Seoul (KR)

(73) Assignee: Korean Institute of Science and Technology, Seoul (KR)

( * ) Notice: Subject to any disclaimer, the term of this patent is extended or adjusted under 35 U.S.C. 154(b) by 890 days.

(21) Appl. No.: 10/805,871

(22) Filed: Mar. 22, 2004

(65) Prior Publication Data

US 2004/0247488 A1    Dec. 9, 2004

(30) Foreign Application Priority Data

Jun. 4, 2003    (KR) .................. 10-2003-0036060

(51) Int. Cl.
  *B01L 3/02*    (2006.01)
(52) U.S. Cl. ..................... 422/100; 422/919
(58) Field of Classification Search ............ 422/100, 422/919
  See application file for complete search history.

(56) References Cited

U.S. PATENT DOCUMENTS

| | | | | |
|---|---|---|---|---|
| 5,845,541 | A * | 12/1998 | Yoneyama | 74/490.12 |
| 6,251,658 | B1 * | 6/2001 | Henderson et al. | 435/285.1 |
| 6,590,139 | B1 * | 7/2003 | Lee et al. | 800/24 |
| 6,661,575 | B1 * | 12/2003 | Yakovenko | 359/393 |
| 2003/0180965 | A1 * | 9/2003 | Yobas et al. | 436/180 |

FOREIGN PATENT DOCUMENTS

JP    11347971    12/1999

OTHER PUBLICATIONS

Machine translation of JP 11-347971 A.*
Fung et al, A 2-D PVDF Force Sensing System for Micro-manipulation and Micro-assembly, May 2002, IEEE, 1489-1494.*
Fung et al, Internet-Based Remote Sensing and Manipulation in Micro Environment, Jul. 2001, IEEE, 695-700.*

(Continued)

*Primary Examiner*—Walter D Griffin
*Assistant Examiner*—Natasha Young
(74) *Attorney, Agent, or Firm*—Ohlandt, Greeley, Ruggiero & Perle, LLP

(57) ABSTRACT

The present invention relates to a smart pipette for bio-cell manipulation which can freely change orientation of a bio-cell subject to the manipulation by using mechanical friction and applying instantaneous impact when penetrating the subject bio-cell while receiving real-time feedback of force/torque information of the bio-cell. Further, the present invention relates to a bio-cell manipulation method and system using a smart pipette, through which a bio-cell may be manipulated upon the application of the force/torque information generated during the cell manipulation to the smart pipette control. According to the present invention, injection position can be recognized precisely and conveniently regardless of the proficiency of the manipulating person. Thus, the bio-cell manipulation may be automated. Further, the smart pipette quantifies force/torque information feedbacked through the sensor unit and compares it with data acquired in advance through experiments on the same bio-cell. Further, through conducting impact driving when necessary, the present invention makes it possible to conduct bio-cell manipulation with minimum physical damage.

18 Claims, 10 Drawing Sheets

OTHER PUBLICATIONS

DeVoe et al, Modeling and Optimal Design of Piezoelectric Cantilever Microactuators, Journal of Microelectromechanical Systems, vol. 6, No. 3, Sep. 1997, 266-270.*

Machine translation of JP 11-347971 A. The Japanese Ptatent was provided in the IDS and has a date of Dec. 21, 1999.*

Aral, F. et al. "Three-Dimensional Bio-Micromanipulation Under the Microscope," IEEE, 2001, pp. 604-609.

Yu, S. et al. "Microbiotic Cell Injection," IEEE, 2001, pp. 620-625.

* cited by examiner

SMART PIPETTE FOR CELL MANIPULATION AND CELL MANIPULATION METHOD FOR USING THE SMART PIPETTE

CROSS-REFERENCE TO RELATED APPLICATION

The entire disclosure of Korean Patent Application No. 10-2003-0036060 filed on Jun. 4, 2003 including specification, claims, drawings and summary is incorporated herein by reference in its entirety.

BACKGROUND OF THE INVENTION

1. Field of the Invention

The present invention relates to a pipette for bio-cell manipulation and, more particularly, to a smart pipette for bio-cell manipulation which can freely change orientation of a bio-cell subject to the manipulation ("Subject Cell") by using mechanical friction and applying instantaneous impact when penetrating the Subject Cell while receiving real-time feedback of force/torque information of the Subject Cell. Thus, according to the present invention, the Subject Cell may be effectively manipulated with minimum distortion, rupture or other deformation.

Further, the present invention relates to a bio-cell manipulation method and system using a smart pipette and, more particularly, to a bio-cell manipulation method and system using a smart pipette, through which a bio-cell may be manipulated upon the application of the force/torque information generated during the cell manipulation to the smart pipette control.

2. Prior Art

The biotechnology through which animal or human body is studied attracts more and more interests these days and currently a lot of research works are ongoing to prevent and cure human disease by discovering the DNA structure of a human body. Recently, a Korean research team discovered first in the world that certain special gene which does not appear in a normal stomach cell becomes active in a stomach cancer cell and protects cancer cell against anticancer medicine.

As a part of the modern science, the biotechnology develops together with nano-technology and information technology, etc., rather than growing independently of other technology field. For example, ultra-small device for disease treatment has been developed through combination of biotechnology, nano-technology and information technology. Accordingly, metabolism trouble is checked by an ultra-small device's moving through blood vessels of a human body and if any problem is discovered, the relevant image is transmitted to an external health diagnosis system or disease treatment system. Further, through communications with the external system, the relevant pathogen may be eliminated directly by the device.

Notwithstanding the recent advance and development in the biotechnology and its combination with various other technology fields, in certain manipulation system such as the ICSI (Intracytoplasmic Sperm Injection) used for the conventional IVF (In Vitro Fertilization), a person must manually operate the manipulator relying exclusively on the visual information obtained from a microscope. In such system, the success rate of the operation largely depends on the skill of the person who manipulates the system and thus for adequate and precise manipulation of the system, the relevant person must receive thorough manipulation training for a substantial time period.

Thus, also in the above-mentioned bio field where the manual manipulation is used, the minute manipulation technology using the micro system needs to be developed and, further, stable and minute bio-cell manipulation method and system is required in which the manipulation may be automated and the manipulating person's proficiency does not make too much difference.

Further, bio-cells can easily be destroyed because bio-cells are not uniform in their shape and are subject to deformation at the time of manipulation. When a live cell is manipulated in liquid, due to the circulation caused by the pipette manipulation, the manipulation environment may be very unstable and thus very high skill is required for manual manipulation of a bio-cell in such case.

Given the foregoing, it is necessary to develop a bio-cell manipulation system and method through which the cell manipulation does not need to be carried out always by a very highly skilled person and through which the cell manipulation may be carried out with stability according to certain settings that can be varied depending on different circumstances.

SUMMARY OF THE INVENTION

The object of the present invention is to provide a bio-cell manipulation system and method using a pipette through which the bio-cell's location may be modified so that even a non-skilled person may easily and precisely recognize the location for bio-cell injection within short time and conduct the injection.

It is another object of the present invention to provide a bio-cell manipulation system and method using a pipette in which the magnitude of force at the time of passing through the boundaries such as the cytoplasmic membrane of the Subject Cell is measured and processed as data through prior experiments, and when the bio-cell is penetrated the force/torque information and the visual information is feed-backed real time from the Subject Cell. Further, according to the present invention, the feed-backed force/torque information is quantified and compared with the data obtained through the prior experiments during the cell manipulation. Thus, the present invention intends to minimize the cell deformation or destruction which may occur during the cell manipulation conducted relying exclusively on the visual information in the related art.

Also, it is another object of the present invention to provide an automated cell manipulation method and system using the real-time feed-backed force/torque information and other information measured in advance.

In order to achieve the above objects, the present invention provides a smart pipette, which, together with a vision unit, a haptic unit, a control unit, a graphic user interface and a holding pipette, constitutes a micro manipulation device, comprising an orientation adjusting unit that changes orientation of the Subject Cell whose location has been fixed by the holding pipette and a sensor unit that obtains force/torque information concerning the Subject Cell and the smart pipette at the time of the cell manipulation.

Preferably, the orientation adjusting unit has the same degree of freedom as the micro manipulation device and may change the orientation of the Subject Cell. Further, preferably, the orientation adjusting unit is made of polymer which is suitable for a living body and the best polymer for this purpose is PDMS (Polydimethylsiloxane).

Preferably, the orientation adjusting unit is located apart from the tip of the pipette in order not to interfere with the penetration into the Subject Cell and it changes orientation of the Subject Cell by using the mechanical friction with the Subject Cell.

Preferably, the orientation adjusting unit changes orientation of the Subject Cell when the holding pipette's force of holding the Subject Cell has been weakened. After the cell manipulation is completed, the Subject Cell is fixed again by the holding pipette.

Preferably, the present invention further comprises a minute driver for minute manipulation of the smart pipette. The minute driver is impact-driven by using the graphic user interface.

Preferably, the sensor unit transmits the force/torque information real time to the haptic unit. Further, preferably, the force/torque information transmitted by the sensor unit is quantified and transmitted to the manipulator through the graphic user interface.

Preferably, the sensor unit is a piezo-electric polymer sensor of a cantilever type and the most preferable piezo-electric polymer is PVDF (Polyvinylidene Fluoride) film.

The present invention provides a bio-cell manipulation method using a smart pipette including a sensor unit, comprising: (a) quantifying force/torque information acquired through the sensor unit during bio-cell manipulation; (b) transmitting the quantified force/torque information to the graphic user interface; and (c) manipulating the bio-cell based upon the force/torque information transmitted in said step (b).

Preferably, the force/torque information quantified in said step (a) is measured by a piezo-electric sensor and then quantified, and then transmitted real time in said step (b). Specifically, the force generated during the bio-cell manipulation is measured by the piezo-electric sensor and the measurement result is provided through a computer monitor, etc.

Preferably, said step (c) comprises: (d) comparing the quantified force/torque information with data acquired through prior experiments; and (e) conducting the bio-cell manipulation based upon the comparison made in said step (d).

Preferably, said step (e) is a step of acquiring information about in which layer of the bio-cell the tip of the smart pipette is located through the comparison made in said step (d). Specifically, if the data acquired through prior experiments conducted on bio-cells that are the same as the bio-cell currently subject to the manipulation show that the force measured when penetrating the first layer is within range 1 and the force measured when penetrating the second layer is within range 2, by comparing the force/torque information quantified in said step (d) with the relevant range, it may be determined which layer is being penetrated.

Further, the present invention provides a bio-cell manipulation system using a smart pipette comprising: a sensory information receiver that acquires sensory information generated between the smart pipette and the bio-cell during the minute manipulation using the smart pipette; and a measuring unit that receives the force/torque information from the sensory information receiver and quantifies such information.

Preferably, the sensory information receiver comprises: a vision unit that acquires visual information of the smart pipette and the bio-cell; and a haptic unit that acquires force/torque information between the smart pipette and the bio-cell.

Preferably, the measuring unit displays the quantified force/torque information using the graphic user interface and expresses the force/torque information as voltage.

Preferably, the present invention further comprises a control unit that controls the smart pipette operation based upon the force/torque information quantified at the measuring unit.

The control unit controls location, operation speed and force required for operation, etc. of the smart pipette.

DETAILED DESCRIPTION OF THE PREFERRED IMPLEMENTATION

Reference will now be made in detail to the preferred embodiments of the present invention as illustrated in the accompanying drawings.

Figure 1A:
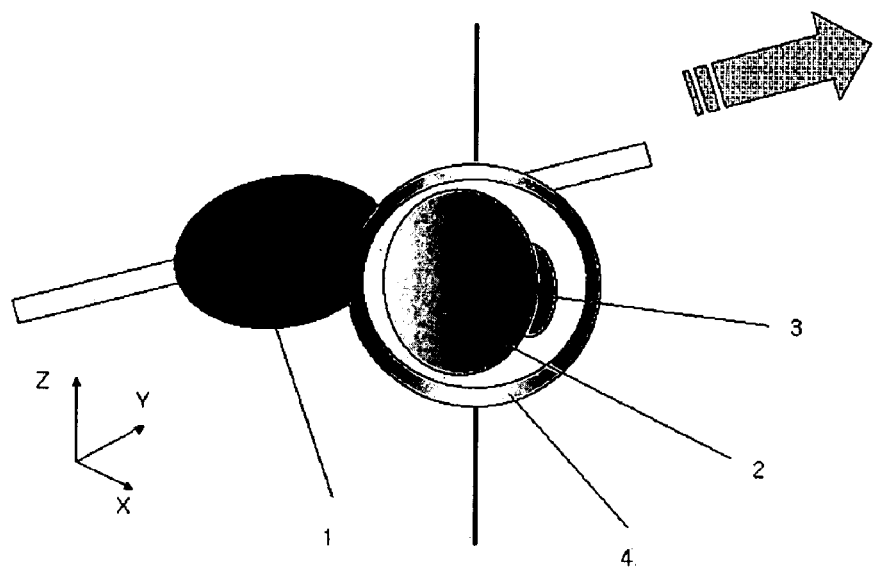
FIG. 1a and FIG. 1b illustrate change of the bio-cell orientation using the smart pipette according to a preferred embodiment of the present invention.
Figure 1B:
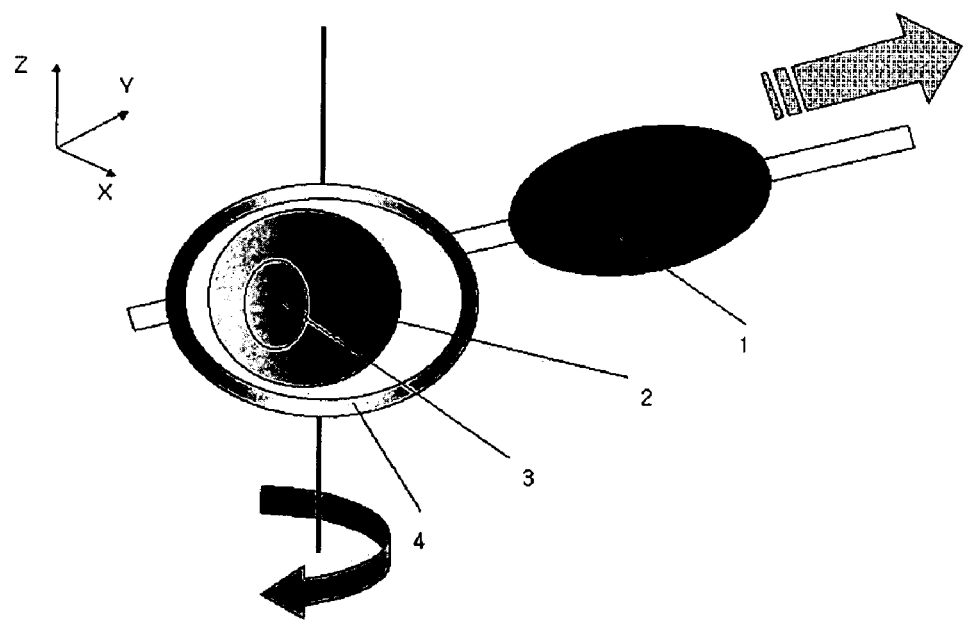

FIG. 1a and FIG. 1b illustrate change of the bio-cell orientation using the smart pipette according to a preferred embodiment of the present invention. FIG. 1a illustrates the orientation adjusting unit 1 of the smart pipette in direct contact with the bio-cell 4 for change of orientation of the bio-cell. The left lower portion of the smart pipette is the tip of the smart pipette. The smart pipette moves to the direction of the axis of the pipette (following the arrow in the drawing). FIG. 1b illustrates changed orientation of the bio-cell 4 as the result of the motion of the smart pipette as illustrated in FIG. 1a. Orientation of the bio-cell 4 may be changed by the smart pipette not only to the direction illustrated in FIG. 1a and FIG. 1b but also to other directions by adjusting direction of the smart pipette's motion and portion of the smart pipette that is in contact with the bio-cell.

As illustrated in FIG. 1a, where the nucleus 2 of the bio-cell 4 (that has the polar body 3 and the nucleus 2) is to be manipulated, if the tip of the smart pipette is not adjacent to the nucleus 2 but is adjacent to the polar body 3 and thus if the polar body 3 blocks the smart pipette's movement to the nucleus 2, it would be necessary to change the orientation of the bio-cell or change the position of the smart pipette to manipulate the bio-cell 4. In this situation, while having the subject bio-cell 4 fixed by the holding pipette (not shown in the drawing), if only the smart pipette is moved to the place appropriate for the manipulation, not to mention the difficulty in re-specifying and changing the position of the smart pipette, the unbalance between direction of the force imposed at the time of the bio-cell penetration and direction of the force supported by the holding pipette increases the possibility of deformation of the subject bio-cell.

Accordingly, it is necessary to adjust the orientation of the subject bio-cell. According to the present invention, as illustrated in FIG. 1a and FIG. 1b, orientation of the bio-cell 4 is adjusted by the mechanical friction between the orientation adjusting unit 1 and the bio-cell 4. Preferably, the orientation adjusting unit 1 is made of material suitable for a living body because its contact with the bio-cell 4 should not have any adverse effect on the bio-cell 4. Further, preferably, the orientation adjusting unit 1 needs to have rough surface because mechanical friction between its surface and the surface of the bio-cell 4 is used for the orientation adjustment. The mechanical friction is generated when the rough surface of the orientation adjusting unit 1 is in gear with the surface of the bio-cell 4. While orientation of the bio-cell is being changed, the holding pipette's force of fixing the bio-cell 4 is decreased and the orientation of the bio-cell 4 is adjusted while it is somewhat free from the holding pipette. When the adjustment of the bio-cell 4's orientation is complete, the bio-cell 4 is fixed again by the holding pipette.

The orientation adjusting unit 1 may be implemented with a polymer such as PDMS (Polydimethylsiloxane) that is suitable for a living body and has appropriately rough surface. The orientation adjusting unit of the smart pipette illustrated in FIG. 1a and FIG. 1b is implemented by coating the polymer to the area close to the tip of the pipette. Preferably, the orientation adjusting unit is located apart from the pipette's tip by certain length (ordinarily, by a radius of the subject bio-cell). If the orientation adjusting unit is located too close to the tip of the pipette, at the time of the bio-cell manipulation such as injection, penetration to the inside of the cell beyond certain depth would be difficult or even if such penetration is possible, the bio-cell's deformation may occur.

Because the smart pipette and the orientation adjusting unit 1 have the same degree of freedom as the micro manipulation device manipulating the bio-cell, the orientation adjusting unit 1 may change orientation of the bio-cell 4 freely in the directions of X, Y and Z axes. The shape of the orientation adjusting unit 1 is not limited to any specific form. It can be implemented to have a cylinder shape, a sphere shape or a cube shape, etc. The shape of the orientation adjusting unit 1 would not make any difference in the change of the bio-cell 4's orientation.

Figure 2A:
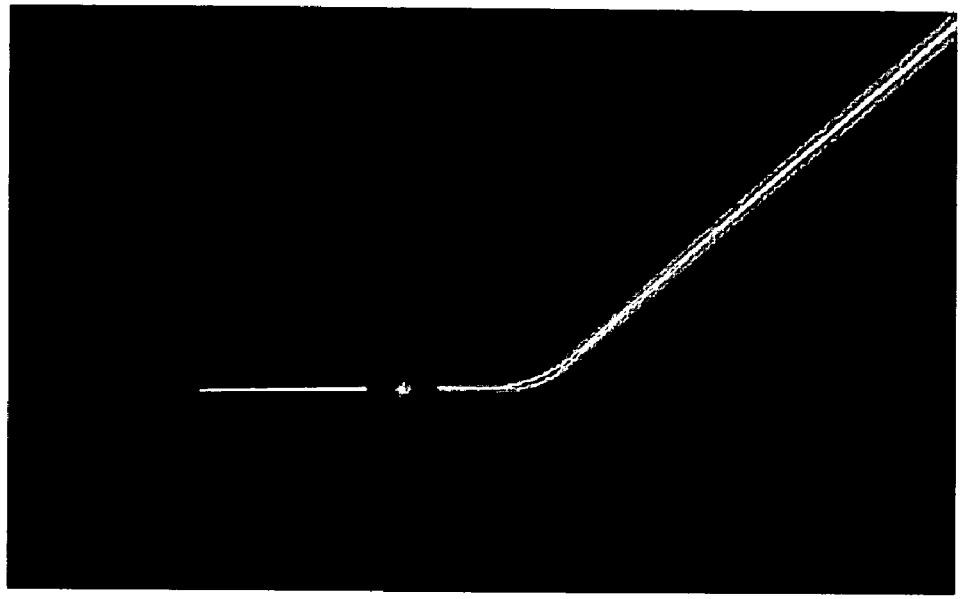
FIG. 2a, FIG. 2b and FIG. 2c illustrate the orientation adjusting unit of the smart pipette according to preferred embodiments of the present invention.
Figure 2B:
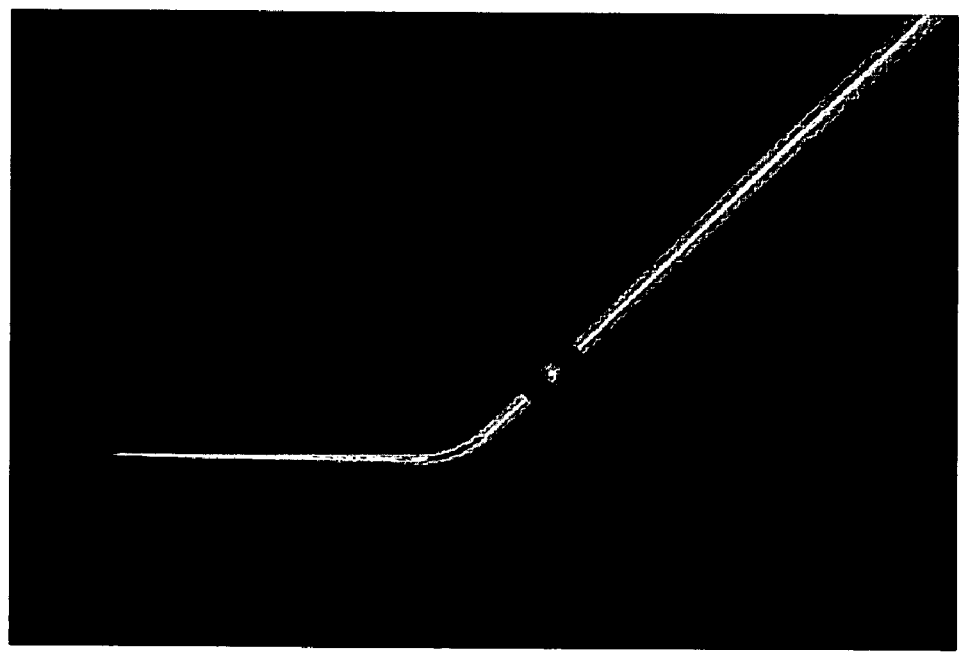
Figure 2C:
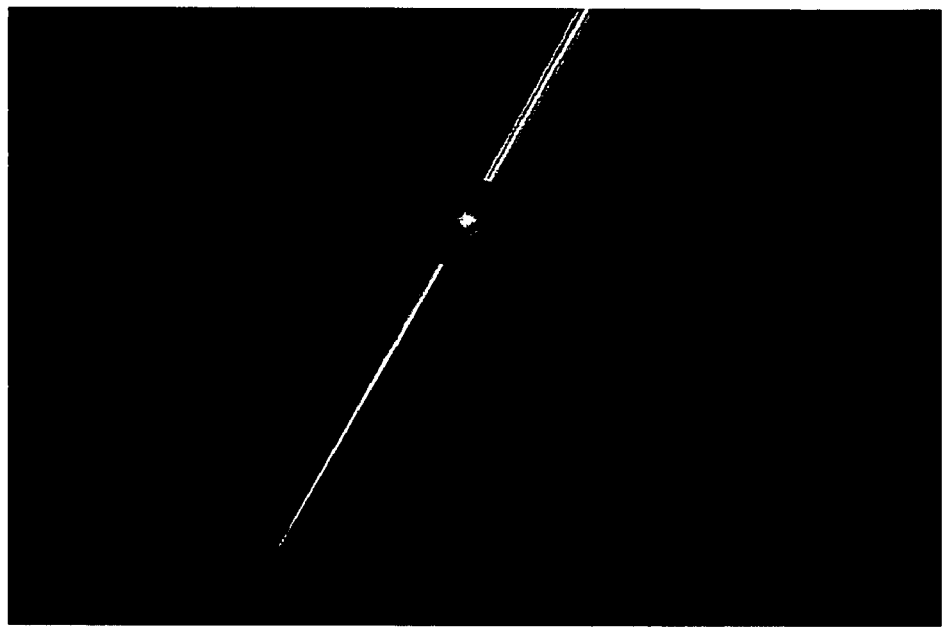

FIG. 2 illustrates orientation adjusting units of the smart pipettes according to the present invention. FIG. 2a illustrates an orientation adjusting unit implemented at the lower part of the bent pipette. FIG. 2b illustrates an orientation adjusting unit implemented at the upper part of the bent pipette. FIG. 2c illustrates an orientation adjusting unit implemented at the tip part of an ordinary pipette.

Preferably, the orientation adjusting unit is located in the area of the pipette which would not be in direct contact with the bio-cell during the injection performed by the pipette. Although all of the orientation adjusting units illustrated in FIG. 2 have sphere shape, it does not mean that the orientation adjusting unit should be of sphere shape.

FIG. 3a through FIG. 3g illustrate the change of the bio-cell orientation and the injection into the bio-cell using the smart pipette according to the present invention.

Figure 3A:
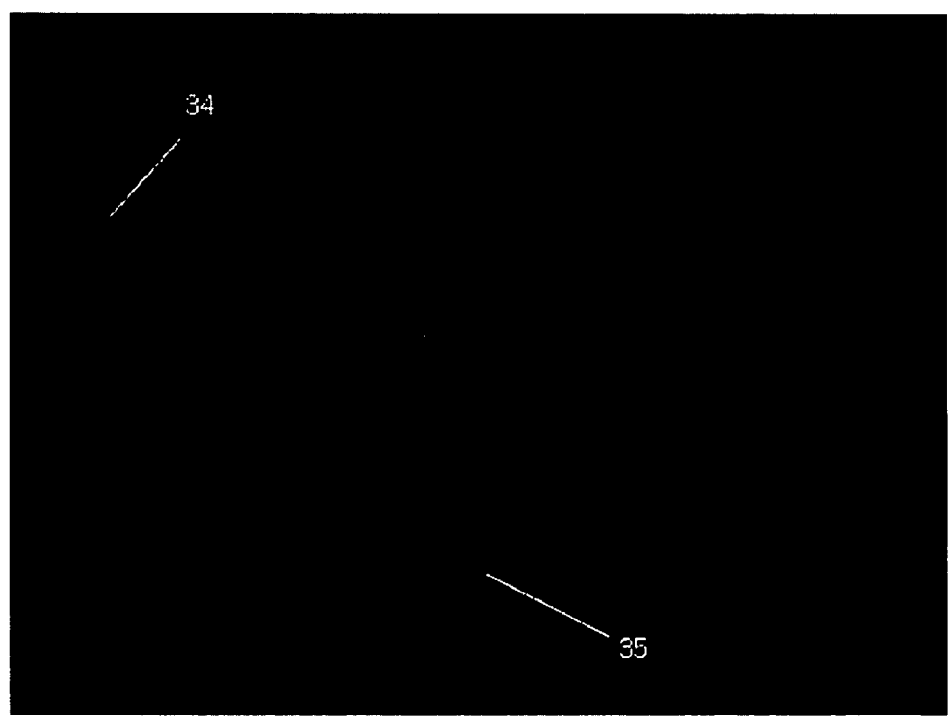
FIG. 3a through FIG. 3g illustrate the change of the bio-cell orientation and the injection into the bio-cell using the smart pipette according to the present invention.
Figure 3B:
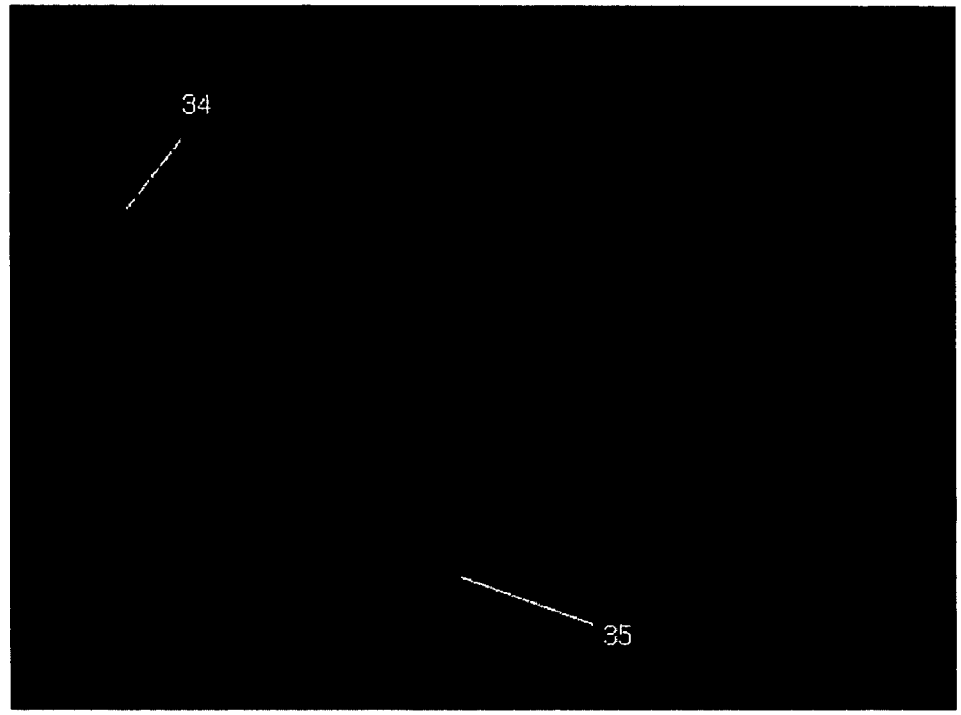
Figure 3C:
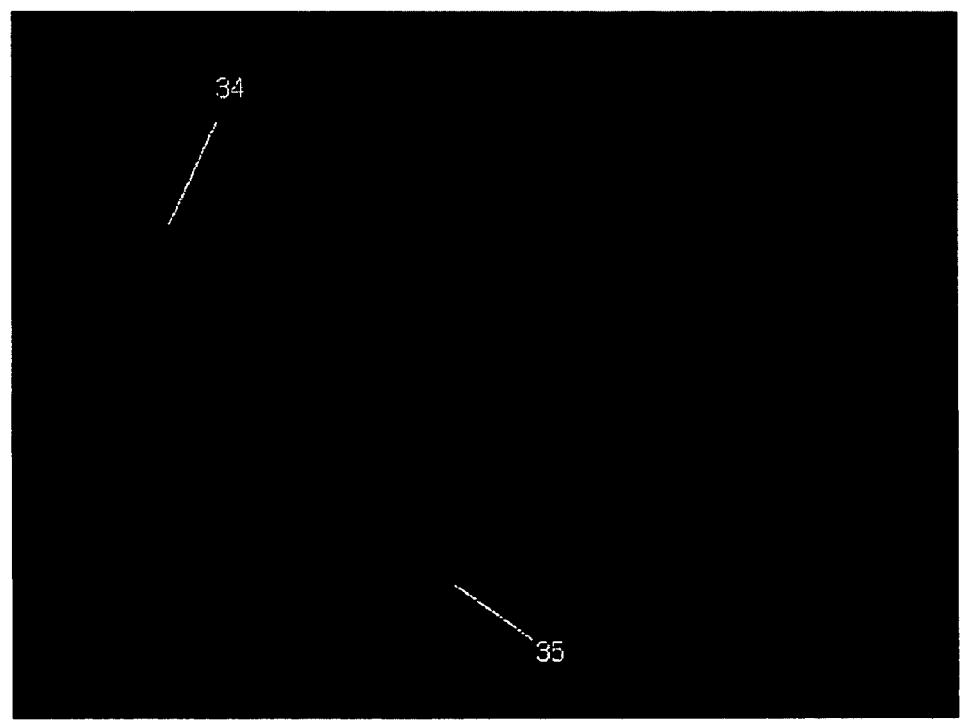

FIG. 3a, FIG. 3b and FIG. 3c illustrate the procedure of changing orientation of a bio-cell using the orientation adjusting unit 35 of the smart pipette. The orientation adjusting unit 35 moves while it is in contact with the bio-cell fixed by the holding pipette 34 and accordingly the bio-cell rotates clockwise.

FIG. 3d, FIG. 3e, FIG. 3f and FIG. 3g illustrate the procedure of injecting the smart pipette (injection pipette) having the orientation adjusting unit 35 into an egg cell of zebrafish.

Figure 3D:
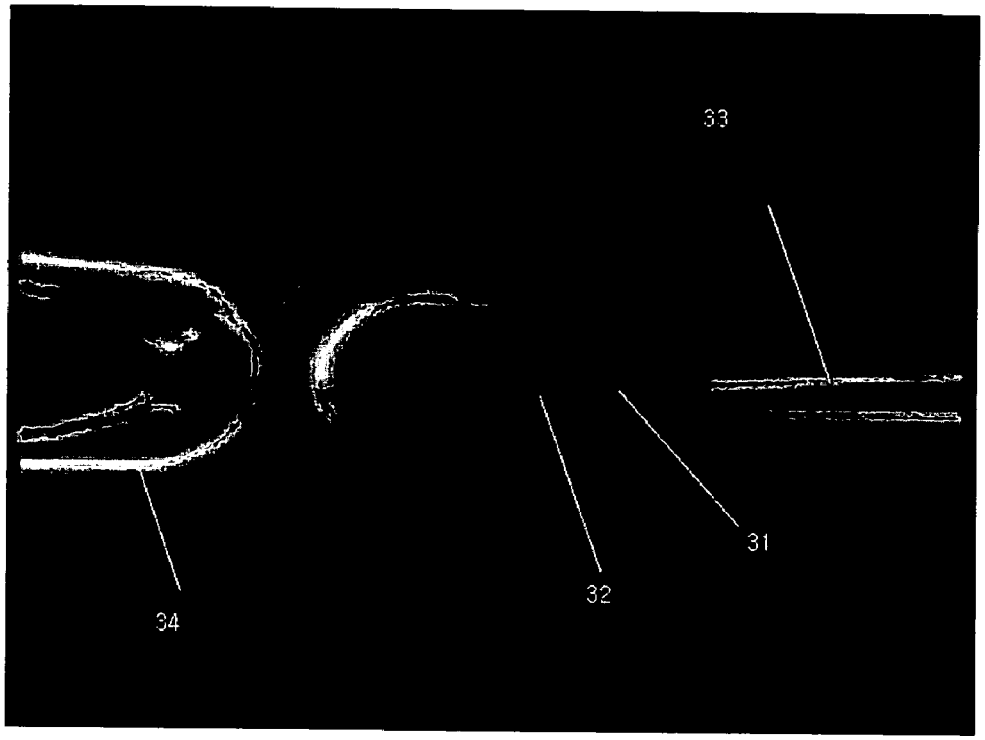
Figure 3E:
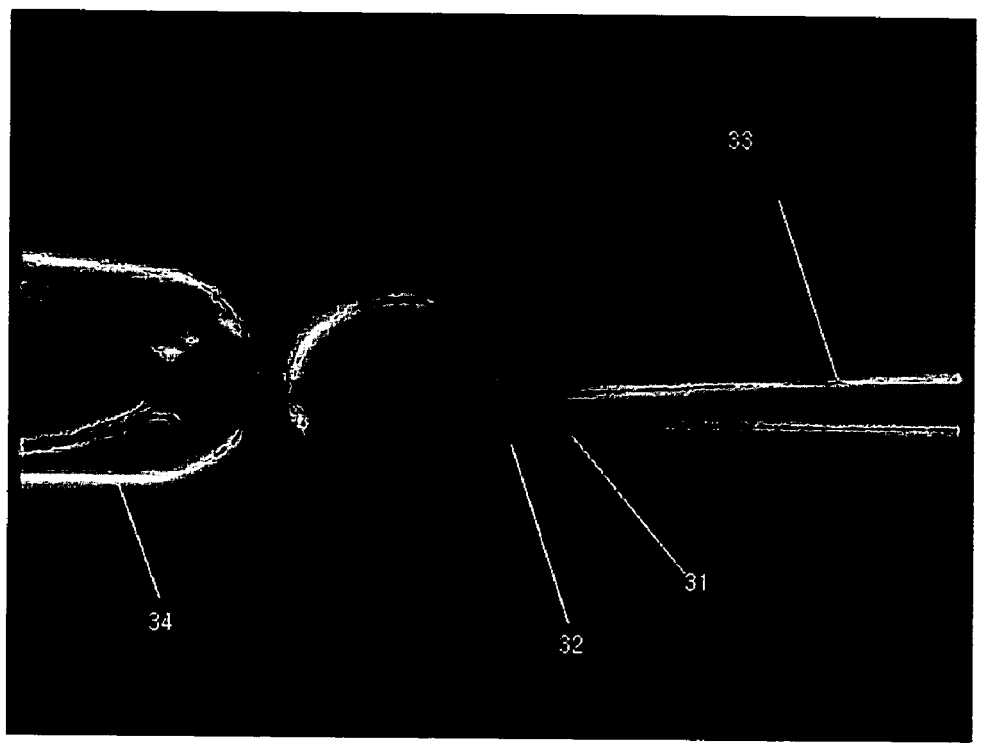
Figure 3F:
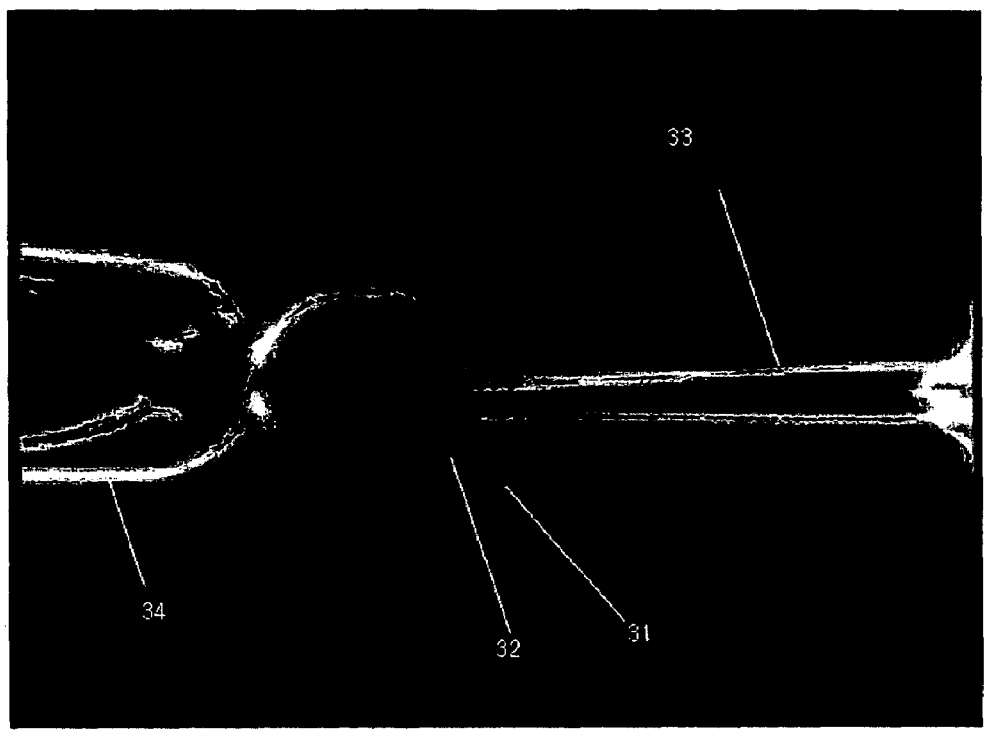
Figure 3G:
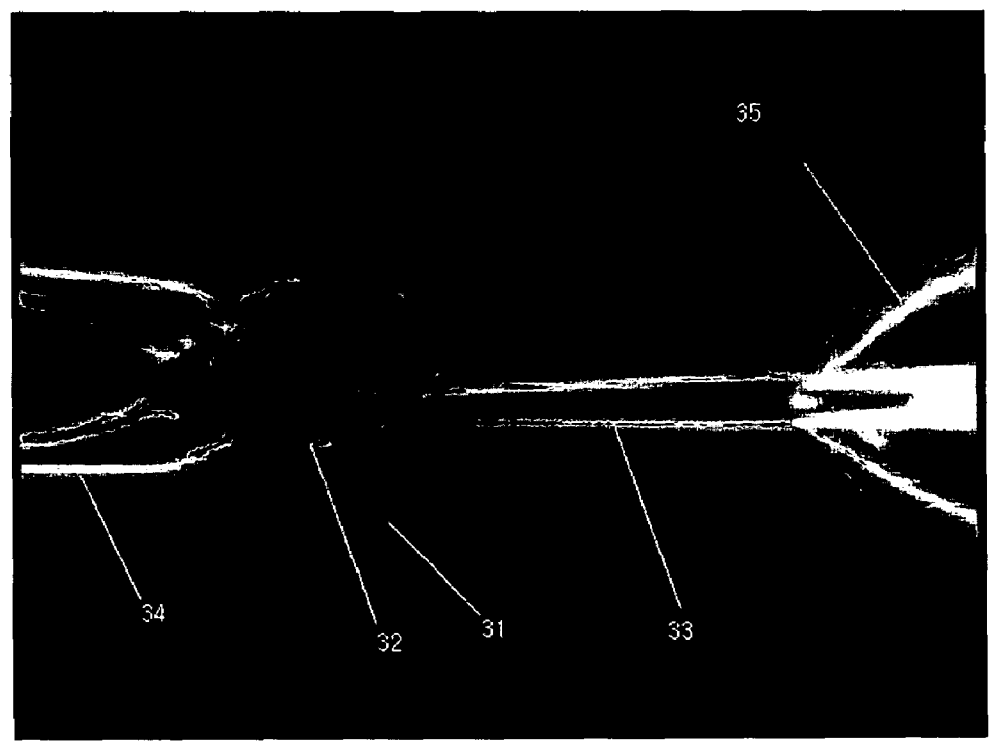

FIG. 3d illustrates the injection pipette 33's approaching chorion 31 of the egg cell fixed by the holding pipette 34 upon having orientation of the cell changed by the orientation adjusting unit (not shown). FIG. 3e illustrates the injection pipette 33's penetrating chorion 31. FIG. 3f illustrates the injection pipette 33's contacting nuclear membrane 32 and starting to penetrate nuclear membrane 32. FIG. 3g illustrates the injection pipette 33's deep penetration into nuclear membrane 32. At the right side of FIG. 3g, the orientation adjusting unit 35 of an oval shape implemented on the injection pipette 33 is illustrated.

If an injection experiment is conducted on an embryo cell of a mouse using a smart pipette according to the present invention, the cell's zona pellucida, cytoplasmic membrane, cytoplasm and nuclear envelop are penetrated in sequence and, thus, the real-time force measurement and haptic feedback according to such sequential penetration are possible. Therefore, it is possible to obtain the exact information on the precise position and the magnitude of force at the time when the tip of the smart pipette penetrates each relevant part of the cell and hence physical damage that may occur during the injection may be reduced. Consequently, the success rate of the injection can be raised.

In the related art, if force is imposed exclusively in reliance on the visual information obtained during the manipulation of the pipette, the stability in bio-cell manipulation is not sufficiently high because the manipulating person's proficiency and experience determine the possibility of penetrating cytoplasmic membrane with the minimum cell deformation. In comparison, the smart pipette according to the present invention comprises a sensor unit that acquires force/torque information generated from the bio-cell during the manipulation and thus it is possible to manipulate the bio-cell with minimum cell deformation by using not only the visual information but also the force/torque information acquired through the sensor unit. Therefore, the stability in the bio-cell manipulation is enhanced.

The force/torque information feed-backed through the sensor unit of the smart pipette makes it possible to recognize which part of the bio-cell is penetrated by the smart pipette. For this purpose, information on the magnitude of force required in penetrating each and every part of the bio-cell is obtained through several previous experiments and arranged as data. Then, at the time of the bio-cell manipulation, the feed-backed force/torque information is quantified and compared with the data. Through this procedure, the bio-cell manipulation using the smart pipette according to the present invention may have a high stability.

Preferably, the sensor unit is made of piezo-electric polymer film called PVDF (Polyvinylidene Fluoride) film. This is to utilize the piezo-electric principle: the fact that electric output signal is generated if mechanical force is imposed. If the sensor unit is made of the PVDF film, the sensor unit will have high linearity and broad bandwidth. Further, signal-to-noise ratio will be high, resulting in high reliability of signal. Additionally, because the sensor unit is made of a polymer material, it will be light and pliable. Moreover, the sensor unit will be stable chemically/mechanically and be suitable for a living body. Therefore, the sensor unit made of the PVDF film is appropriate as a sensor of bio-cell manipulation force.

Figure 4:
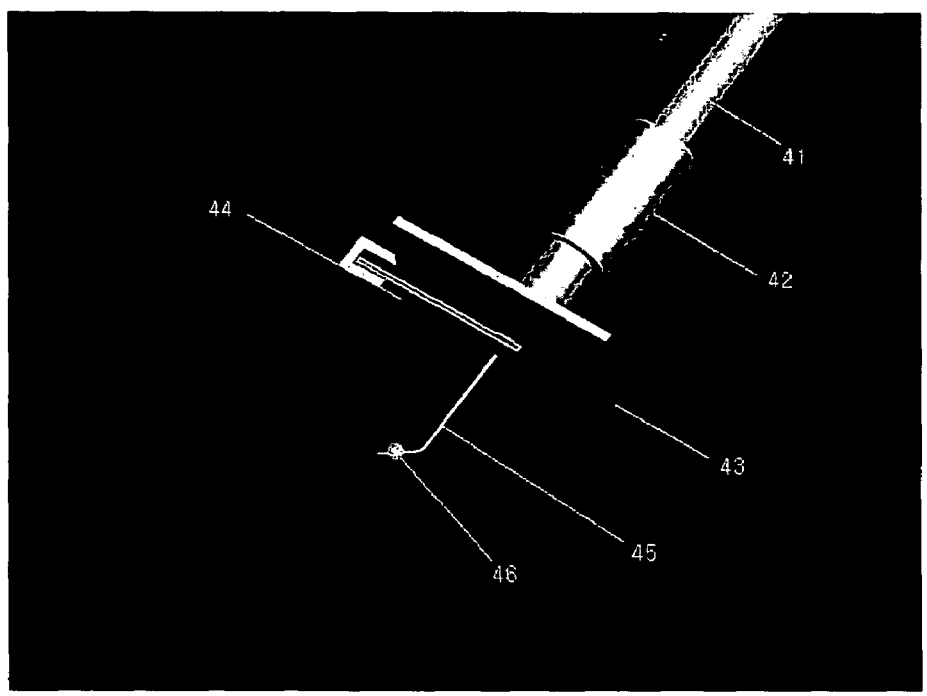
FIG. 4 illustrates the smart pipette according to the first preferred embodiment of the present invention.

FIG. 4 illustrates a smart pipette according to the first embodiment of the present invention.

The smart pipette according to the first embodiment of the present invention comprises a capillary holder 41, a tip holder 42, a membrane plane 43, a PVDF sensor 44 and a pipette 45, combined in sequence. The smart pipette comprises an orientation adjusting unit 46 which is a polymer coated at the tip portion of the smart pipette.

For a bio-cell manipulation using the smart pipette (e.g., for a bio-cell injection), orientation of the bio-cell is changed by using the orientation adjusting unit 46 and then the bio-cell penetration is conducted. At this time, magnitude of the force detected by the PVDF sensor 44 is transmitted to the bio-cell manipulating person through the haptic device (not shown in the drawing) connected to the PVDF sensor 44. The magnitude of the force sensed by the sensor is quantified through the graphic user interface and provided to the bio-cell manipulator. Then, the bio-cell manipulator conducts the bio-cell injection in accordance with the magnitude of the strength, minimizing the bio-cell deformation and possible damage to the bio-cell that may occur during the injection. Moreover, if an actuator is installed, microscopic driving and impact driving of the smart pipette can be conducted and thus the stability of the bio-cell manipulation may be even further enhanced.

Figure 5:
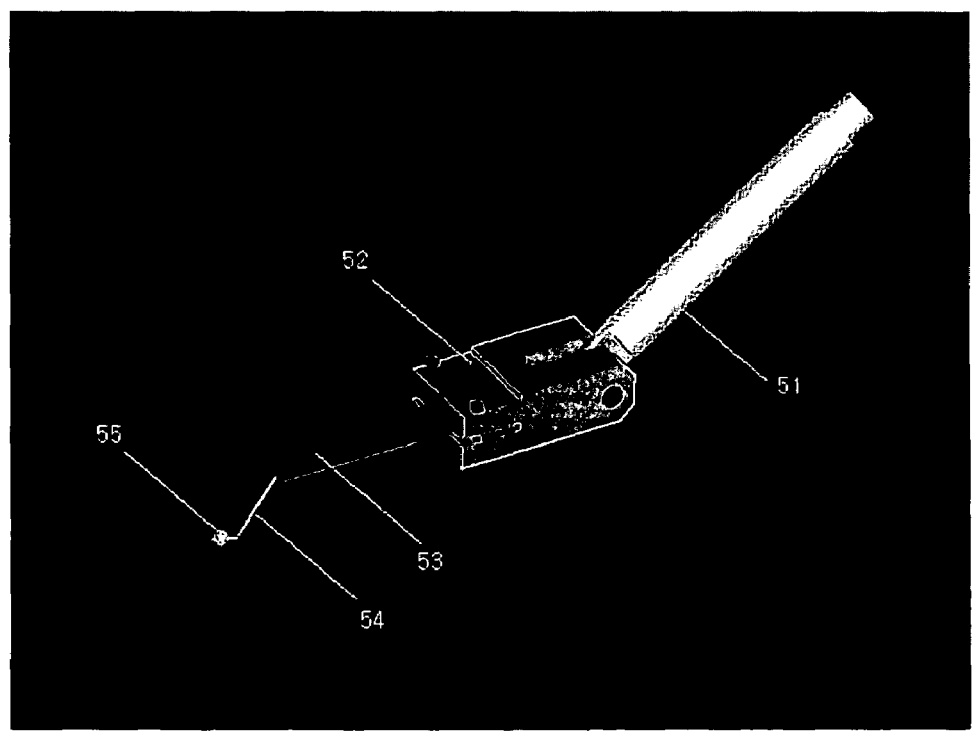
FIG. 5 illustrates the smart pipette according to the second preferred embodiment of the present invention.

FIG. 5 illustrates a smart pipette according to the second embodiment of the present invention.

As shown in FIG. 5, the smart pipette comprises a connecting rod 51, a clamping structure 52, a piezo-electric actuator 53 and a pipette 54, combined in sequence. A polymer is coated at the tip portion of the pipette to be an orientation adjusting unit 55. In this smart pipette, of the two surfaces of the piezo-electric actuator 53, a PVDF sensor is attached to the surface that is connected to the pipette 54. Parylene is coated on the PVDF sensor. Thus, the PVDF sensor becomes an insulating layer against electric/mechanical vibration and becomes suitable for a living body. Further, the parylene layer works as a heat insulator guaranteeing the pyroelectricity which is the characteristic of the electricity generation by heat of the PVDF sensor.

The piezo-electric actuator 53 of the smart pipette plays the roles of a driver and a sensor at the same time. Through the force/torque information acquired real time during the bio-cell manipulation, it is possible to recognize what portion of the bio-cell the tip of the pipette is penetrating. The force/torque information may be quantified. The quantified force/torque information is feed-backed real time and then compared with the force/torque information acquired through previous experiments of the bio-cell penetration. By using this method, the impact driving at the appropriate time with the appropriate force becomes possible. Alternatively, the pipette may be moved close to the subject bio-cell by the manipulator's manual manipulation based upon visual information and force/torque information and then, for the penetration of the relevant layer within the subject bio-cell, the impact driving can be conducted by transmitting control commands through the graphic user interface. Consequently, the subject bio-cell may be penetrated within short time with the appropriate force. Thus, the physical damage to the subject bio-cell may be minimized.

The location of the orientation adjusting unit at the tip portion of the smart pipette shown in FIG. 4 and FIG. 5 may vary as illustrated in FIG. 2a, FIG. 2b and FIG. 2c. The smart pipette may be driven by oil hydraulic driving method or air hydraulic driving method.

Figure 6:
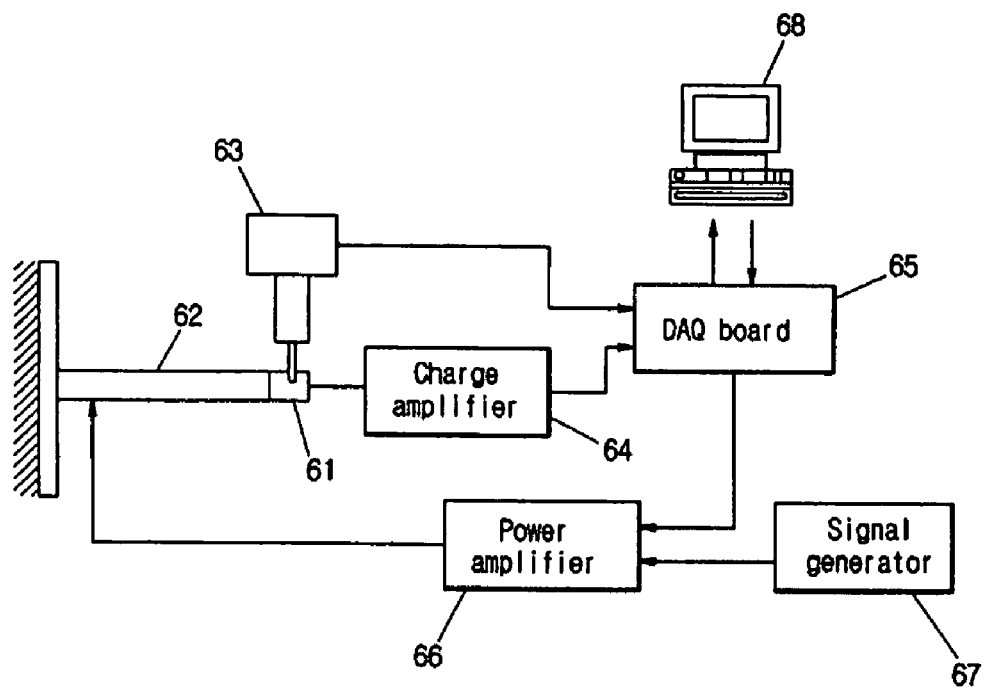
FIG. 6 illustrates a system to measure a PVDF sensor response to the mechanical load imposed upon the piezoelectric actuator comprising the PVDF sensor.

FIG. 6 illustrates a system to measure a PVDF sensor's response to the mechanical load imposed upon the piezo-electric actuator comprising the PVDF sensor.

Said measuring system comprises a PVDF sensor 61, a piezo-electric actuator 62, a load cell 63, a charge amplifier 64, a DAQ board 65, a power amplifier 66 and a signal generator 67. Signal generated by the signal generator 67 is amplified by the power amplifier 66 and drives the piezo-electric actuator 62. When the piezo-electric actuator 62 receives mechanical load, it outputs the mechanical load in the form of electric power. The mechanical load is measured by the load cell 63 and, at the same time, electric charge is outputted to the charge amplifier 64 connected to the PVDF sensor 61. The electric charge outputted from the PVDF sensor 61 is amplified at the charge amplifier and further processed by using the low frequency band filter so that noise is eliminated from the amplified signal.

The output voltage from the charge amplifier 64 and the output voltage from the load cell 63 are measured by the DAQ (Data Acquisition) board 65. The result shows that if the mechanical load increases, there also is linear increase in the voltage outputted from the PVDF sensor 61.

Preferably, the PVDF sensor 61 may be implemented to be a cantilever type. Depending on how the cantilever type PVDF sensor is designed, the PVDF sensor would have different measuring range and resolution. Thus, it is possible to design a sensor that is appropriate for physical characteristics of the subject bio-cell.

For example, if a cantilever PVDF sensor is designed to have the size of 2⊥ 6 mm (44 μm thick), the resulting sensitivity is 0.0395 mN/mV and the resolution is approximately 40 μN.

Figure 7:
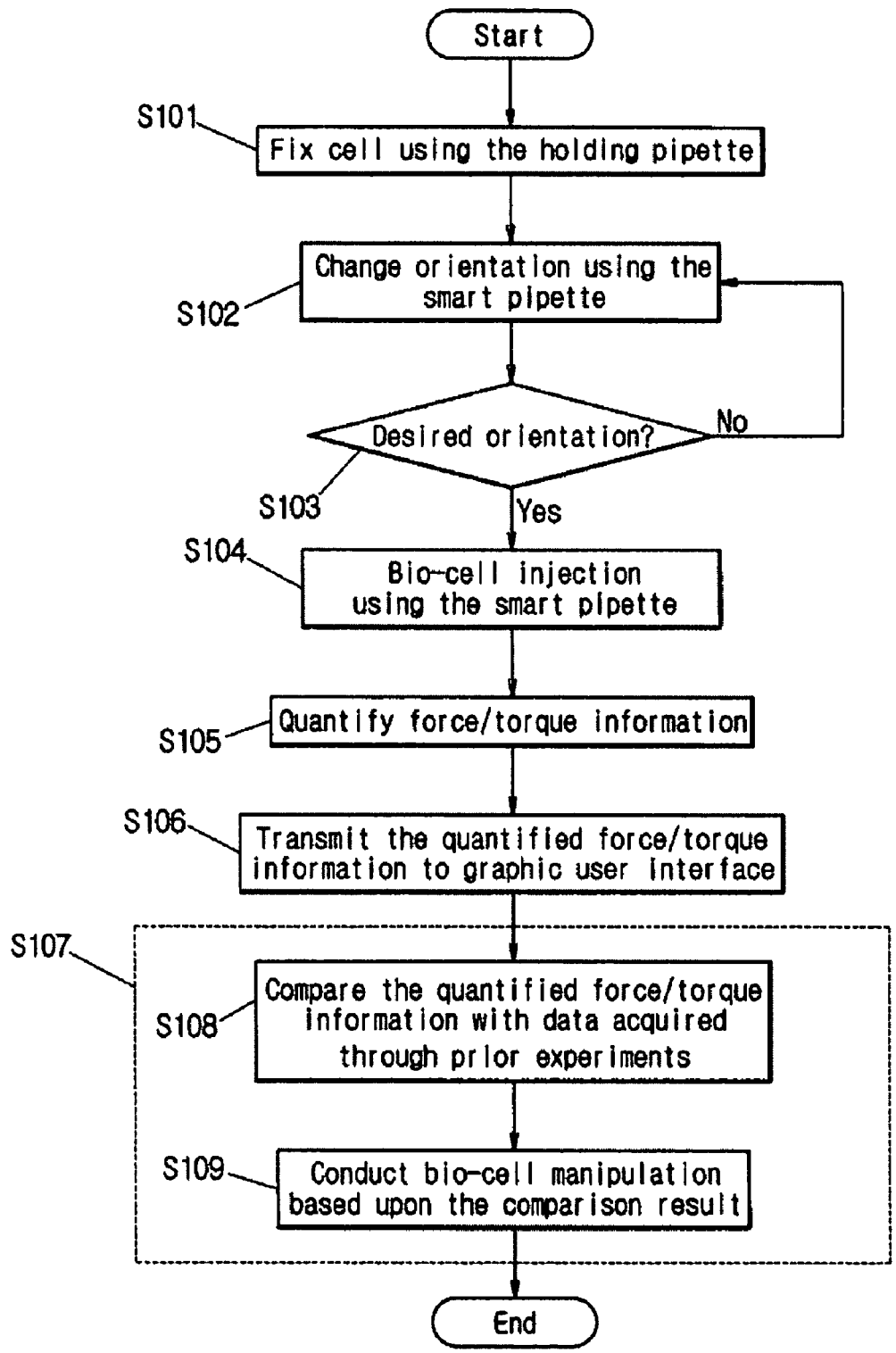
FIG. 7 is a flow chart illustrating the bio-cell manipulation method using the smart pipette according to a preferred embodiment of the present invention.

FIG. 7 is a flow chart illustrating the bio-cell manipulation method using the smart pipette according to a preferred embodiment of the present invention.

For the bio-cell manipulation using the smart pipette, first, the bio-cell is fixed by the holding pipette (S101) and then orientation of the bio-cell is adjusted so that the bio-cell would have the orientation that is suitable for manipulation (S102). The bio-cell orientation change in said step S102 is made by having the orientation adjusting unit at the tip portion of the smart pipette contact the bio-cell. The orientation adjusting unit is preferably of a material that is suitable for a living body and has somewhat rough surface. The bio-cell's force that fixes the bio-cell is weakened while the bio-cell's orientation change is made. After the bio-cell's orientation change, the bio-cell is observed with a micro camera or an optical microscope, etc. and through such observation it is determined whether the orientation has been changed as intended (S103). If the orientation has not been changed appropriately, the orientation change is performed again (S102). If the bio-cell's orientation has been changed as intended, the injection into the bio-cell is conducted using the smart pipette (S104). Force/torque information generated during the bio-cell injection is quantified (S105). The quantified force/torque information is transmitted to the graphic user interface (S106). Then, the bio-cell manipulation is conducted using the force/torque information transmitted to the graphic user interface (S107). The quantified force/torque information that has been transmitted to the graphic user interface is compared with data acquired through prior experiments (S108). The bio-cell manipulation is performed based upon the result of the comparison (S109).

For example, after the orientation change, the bio-cell injection may be performed as follows. If the data acquired through prior experiments conducted on the same bio-cell as the subject bio-cell show that the magnitude of force measured when penetrating the first layer (e.g., chorion) is within range 1 and the magnitude of force measured when penetrating the second layer (e.g., cytoplasmic membrane) is within range 2, it is determined which range of these two ranges the quantified force/torque information belongs to. Accordingly, it is determined which layer is being penetrated. Based upon the comparison result, the bio-cell manipulation can be performed by increasing the force imposed on the smart pipette or by impact-driving the smart pipette. Preferably, the unit of quantified force/torque information is the same as that of data acquired in advance.

Figure 8:
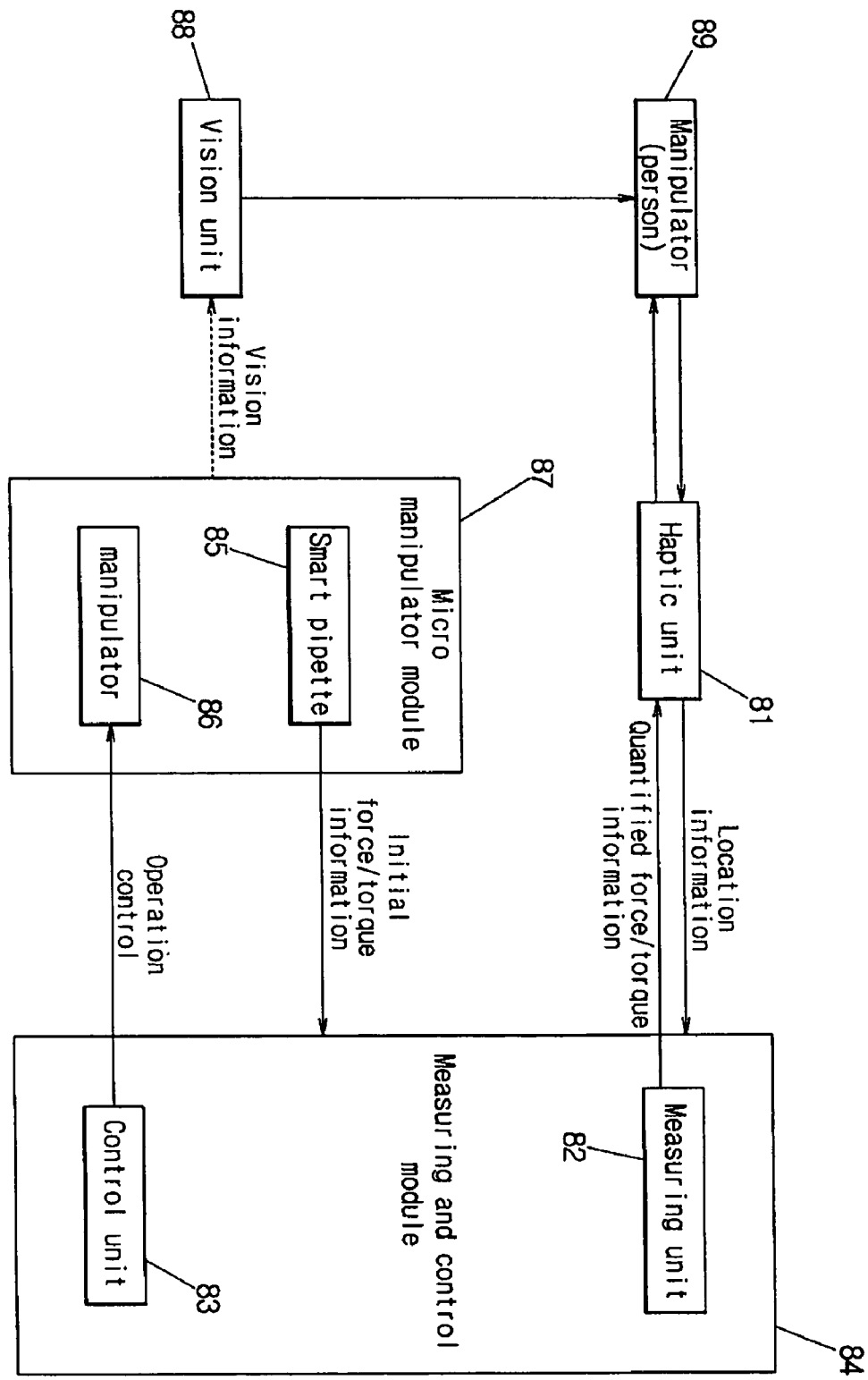
FIG. 8 illustrates the bio-cell manipulation method and system using the smart pipette according to a preferred embodiment of the present invention.

FIG. 8 illustrates the bio-cell manipulation method and system using the smart pipette according to a preferred embodiment of the present invention. The bio-cell manipulation system using the smart pipette illustrated in FIG. 8 comprises a haptic unit 81, a measuring and control module 84, a micro manipulator module 87, a vision unit and a manipulating person 89. The measuring and control module 84 comprises a measuring unit 82 and a control unit 83. The micro manipulator module 87 comprises the smart pipette 85 and a manipulator 86.

For bio-cell manipulation using the smart pipette, visual information and force/torque information generated during the bio-cell manipulation is transmitted to the vision unit 88 and the haptic unit 81 that are receivers of sensory information in the present invention. The visual information regarding the smart pipette is captured by an optical microscope or a micro camera, etc. and is transmitted to the vision unit 88. The transmitted visual information is provided to the manipulating person 89 through a computer monitor, etc., for the manipulating person 89's recognition of the current circumstances of the manipulation.

On the other hand, the force/torque information generated during the bio-cell manipulation using the smart pipette is transmitted to the measuring and control module 84. The force/torque information is quantified by the measuring unit 82 of the measuring and control module 84. The quantified force/torque information is transmitted to the graphic user interface and at the same time transmitted to the haptic unit 81. Thus, the manipulating person 89 may personally feel the force/torque information transmitted to the haptic unit 81 and perceive the magnitude of the force/torque information objectively. This is possible in the present invention because it uses the fact that as the mechanical load increases, there is corresponding linear increase in the response of the PVDF sensor, which is illustrated by the measurement of the PVDF sensor's response to the mechanical load imposed on the piezo-electric actuator comprising the PVDF sensor. The force/torque information may be expressed in voltage as the response of the PVDF sensor is expressed in voltage.

Force/torque information at the time of penetrating relevant layers of a bio-cell is measured by using a piezo-electric sensor, etc. in several experiments conducted in advance. The measured force/torque information is accumulated as data and compared with the force/torque information transmitted from the haptic unit 81 during the manipulating person 89's bio-cell manipulation. Upon the comparison, the magnitude of force/torque information that the manipulating person acquires during the bio-cell manipulation is determined and thus the manipulating person may recognize in which layer the bio-cell manipulation is being performed. Accordingly, more reliable determination can be made according to the present invention than in other cases where only visual information is used.

In other words, the data prepared in advance become criteria in conducting bio-cell manipulation. The control unit compares the quantified force/torque information and said data and makes determination on driving of the smart pipette (e.g., whether the smart pipette will be impact-driven, when the impact driving will be conducted, etc.) based upon the comparison result. Further, the control unit controls the operation of the manipulator according to the location information transmitted from the haptic unit. In this manner, the location, operation speed and force of the smart pipette are controlled.

The determination on the impact driving is made based upon the above-described comparison rather than in reliance on the personal perception of the manipulating person. Therefore, this process may be automatically controlled using a comparison program and eventually the bio-cell manipulation may be automated.

The foregoing embodiments of a smart pipette and bio-cell manipulation method and system using the smart pipette are merely exemplary and are not to be construed as limiting the present invention. Many alternatives, modifications and variations will be apparent to those skilled in the art.

EFFECT OF THE INVENTION

According to the present invention, because orientation of the subject bio-cell is changed by the orientation adjusting unit so that injection position can be recognized precisely and conveniently regardless of the proficiency of the manipulating person. Thus, the bio-cell manipulation may be automated.

Further, the smart pipette according to the present invention quantifies force/torque information feed-backed through the sensor unit and compares it with data acquired in advance through experiments on the same bio-cell. Thus, the manipulation process may be monitored exactly. Further, through conducting impact driving when necessary, the present invention makes it possible to conduct bio-cell manipulation with minimum physical damage.

What is claimed is:

1. A smart pipette for bio-cell manipulation, comprising:
  a holding pipette that fixes a location of a bio-cell;
  an injection pipette that manipulates the bio-cell;
  an orientation adjusting unit formed on the injection pipette, which contacts the bio-cell and changes an orientation of the bio-cell using friction with the bio-cell; and
  a sensor unit that obtains force/torque information concerning the bio-cell and the smart pipette at the time of the bio-cell manipulation.

2. The smart pipette for bio-cell manipulation according to claim 1, wherein the orientation adjusting unit has same degree of freedom as the smart pipette.

3. The smart pipette for bio-cell manipulation according to claim 1, wherein the orientation adjusting unit is suitable for a living body.

4. The smart pipette for bio-cell manipulation according to claim 1, wherein the orientation adjusting unit is a polymer.

5. The smart pipette for bio-cell manipulation according to claim 1, wherein the orientation adjusting unit is located apart from a tip of the injection pipette at least by certain length that would make said orientation adjusting unit not interfere with penetration into the bio-cell.

6. The smart pipette for bio-cell manipulation according to claim 1, wherein the orientation adjusting unit changes orientation of the bio-cell when the holding pipette's force that holds the bio-cell has been weakened.

7. The smart pipette for bio-cell manipulation according to claim 1, wherein the sensor unit is a piezo-electric polymer sensor.

8. The smart pipette for bio-cell manipulation according to claim 1, wherein the sensor unit is a cantilever type.

9. The smart pipette for bio-cell manipulation according to claim 2, wherein the orientation adjusting unit changes orientation of the bio-cell to directions of x, y or z axes.

10. The smart pipette for bio-cell manipulation according to claim 4, wherein the polymer is polydimethylsiloxane (PDMS).

11. The smart pipette for bio-cell manipulation according to claim 7, wherein the piezo-electric polymer is polyvinylidene fluoride (PVDF) film.

12. The smart pipette for bio-cell manipulation according to claim 1, further comprising a minute driver for minute manipulation of the smart pipette.

13. The smart pipette for bio-cell manipulation according to claim 12, wherein the minute driver conducts impact driving using a graphic user interface.

14. A bio-cell manipulation method using a smart pipette, comprising:
  (a) fixing the location of a bio-cell;
  (b) changing the orientation of the bio-cell using friction between the bio-cell and an orientation adjusting unit formed on an injection pipette;
  (c) manipulating the bio-cell using the injection pipette;
  (d) quantifying force/torque information acquired through a sensor unit during said step of manipulating;
  (e) transmitting the quantified force/torque information to a graphic user interface; and
  (f) manipulating the bio-cell based upon the force/torque information transmitted in said step (e).

15. The bio-cell manipulation method using a smart pipette according to claim 14, wherein the force/torque information quantified in said step (d) is measured by a piezo-electric sensor and then quantified.

16. The bio-cell manipulation method using a smart pipette according to claim 14, wherein in said step (e), the force/torque information is transmitted real time.

17. The bio-cell manipulation method using a smart pipette according to claim 14, wherein said step (f) comprises: (g) comparing the quantified force/torque information with data acquired through prior experiments; and (h) conducting the bio-cell manipulation based upon the comparison made in said step (g).

18. The bio-cell manipulation method using a smart pipette according to claim 17, wherein said step (h) is a step of acquiring information about in which layer of the bio-cell a tip of the smart pipette is located based upon the comparison made in said step (g).

* * * * *